United States Patent [19]

Kaplan et al.

[11] 4,451,447

[45] May 29, 1984

[54] PHARMACEUTICAL FORMULATIONS

[75] Inventors: Murray A. Kaplan, Syracuse; Alphonse P. Granatek, Baldwinsville, both of N.Y.

[73] Assignee: Bristol-Myers Company, New York, N.Y.

[21] Appl. No.: 334,206

[22] Filed: Dec. 24, 1981

Related U.S. Application Data

[63] Continuation of Ser. No. 135,373, Mar. 31, 1980, abandoned.

[51] Int. Cl.³ .............................................. A61K 33/24
[52] U.S. Cl. .................................................... 424/131
[58] Field of Search ................................ 424/131, 287

[56] References Cited

FOREIGN PATENT DOCUMENTS 2021996 12/1979 United Kingdom .

OTHER PUBLICATIONS

Rosenberg et al., Nature 205, pp. 698–699 (1965).
Rosenberg et al., Nature 222, pp. 385–386 (1969).
Kauffman et al., Inorganic Synthesis, McGraw-Hill Book Co., N.Y., pp. 239–245 (1963).
Breusova–Baidala et al., Akademia Nauk, SSSR, No. 6, pp. 1239–1242 (1974).
Reishus et al., J. of Am. Chem. Soc., 83 pp. 2457–2462 (1961).
Rozencweig et al., Annals of Internal Med., 86 pp. 803–812 (1977).
Talley et al., Cancer Chemotherapy Reports 57, pp. 465–471 (1973).
Rossof et al., Cancer 30, pp. 1451–1456 (1972).
Haldelsman et al., Clinical Brochure, Cis-Platinum (II) Diamminedichloride(NSC-119875) pp. 1–5 & 31–32 (8–1974).
Hendry et al., Anaesthesia, 1977, vol. 32, pp. 996–999.

*Primary Examiner*—Jerome D. Goldberg
*Attorney, Agent, or Firm*—Richard R. Lloyd

[57] ABSTRACT

Stable concentrated solutions of cisplatin in a solvent comprising polyethylene glycol or methoxy polyethylene glycol, or a mixture thereof, plus water and a nontoxic pharmaceutically acceptable source of chloride ion.

3 Claims, No Drawings

PHARMACEUTICAL FORMULATIONS

CROSS-REFERENCE TO RELATED APPLICATION

This application is a continuation of our prior, copending application Ser. No. 135,373, filed Mar. 31, 1980 and now abandoned.

BACKGROUND OF THE INVENTION

1. Field of the Invention

This invention relates to stable, concentrated solutions of cisplatin in aqueous polyethylene glycol, methoxy polyethylene glycol, or mixtures thereof, containing a source of chloride ion.

2. Description of the Prior Art

The platinum compounds are a unique group of compounds in the antineoplastic group of agents. They were first noted to have an antibiotic effect by Rosenberg and his colleagues in 1965 [Rosenberg, B. et al., *Nature* (London), 205, 698–699 (1965)] and subsequently found by Rosenberg and his colleagues to be potent antitumor agents in animals [Rosenberg, B. et al., *Nature* (London), 222, 385–386 (1969)].

Structurally they represent a complex formed by a central atom of platinum and surrounded by various arrangements of chlorine atoms or ammonia groups in either a cis or trans planar relationship. Two of the more commonly studied platinum compounds are diagrammed below:

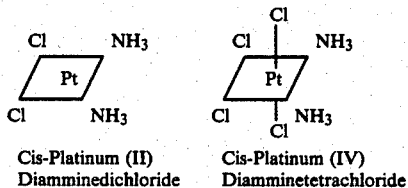

Cis-Platinum (II) Diamminedichloride

Cis-Platinum (IV) Diamminetetrachloride

As can be seen, the compound cis-platinum (II) diamminedichloride has all its chloro and amino groups in a single plane. This compound, now known by the United States Adopted Name (USAN) cisplatin, has been synthesized according to the following reaction:

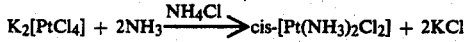

[see Kauffman, G. B. et al., in *Inorganic Synthesis*, J. Kleinberg (Ed.), pages 239–245, McGraw-Hill Book Co., Inc., New York, 1963].

Breusova-Baidala, Y. G. et al., in *Akademia Nauk SSSR*, No. 6, pp. 1239–1242 (June 1974), discuss the slow isomerization of cis-platinum (II) diamminedichloride in aqueous solution to the trans form.

Reishus, J. W. and Martin, D. S., in *Journal of the American Chemical Society*, 83, 2457–2462 (1961), describe the acid hydrolysis of cisplatin at 25° C. and 35° C. These studies were conducted in aqueous solutions at concentrations of $1.5 \times 10^{-3}$ M, $2.5 \times 10^{-3}$ M and $5.0 \times 10^{-3}$ M, which correspond to 0.45, 0.75 and 1.5 mg/ml, respectively. The authors state that there was some ambiguity in locating the origin (i.e. "zero point") for the hydrolysis curves because the samples required from 10 to 30 minutes to dissolve completely even at those low concentrations.

Rozencweig, M. et al., in *Annals of Internal Medicine*, 86, 803–812 (1977), review the results of various preclinical and clinical investigations of the use of cisplatin in experimental tumors in animals as well as various types of human tumors. They point out that the investigational drug, available to qualified investigators through the Investigational Drug Branch of the Cancer Therapy Evaluation Program of the National Cancer Institute, was supplied as a white lyophilized powder in vials containing 10 mg of cisplatin, 90 mg of sodium chloride, 100 mg of mannitol (U.S.P.) and hydrochloric acid for pH adjustment. When reconstituted with 10 ml of sterile water for injection (U.S.P.), each ml of the resulting solution would contain 1 mg of cisplatin, 10 mg of mannitol and 9 mg of NaCl.

Talley, R. W. et al., in *Cancer Chemotherapy Reports*, 57, 465–471 (1973), describe the results of their Phase I clinical study of the use of cisplatin in the treatment of 65 human patients with a wide variety of neoplasms. As in the preceding publication, the drug was supplied to them by the National Cancer Institute in vials containing 10 mg of cisplatin, 90 mg sodium chloride and 100 mg of mannitol, for reconstitution with 10 ml of sterile water.

Rossof, A. H. et al., in *Cancer* 30, 1451–1456 (1972), describe the results of their use of cisplatin in the treatment of 31 human patients with a variety of tumor types. They state that the drug supplied by the National Cancer Institute was manufactured by Ben Venue Laboratories, Inc. and contained, per vial, 10 mg of cisplatin, 10 mg (sic) of mannitol and 9 mg (sic) of NaCl, and that the yellowish-white powder dissolved readily in 8–10 ml of sterile water.

Certain information concerning the chemistry and pharmaceutical formulation of cisplatin are given on pages 1–5 and 31–32 of the publication entitled "CLINICAL BROCHURE, CIS-PLATINUM (II) DIAMMINEDICHLORIDE (NSC-119875)", H. Haldelsman et al., Investigational Drug Branch, Cancer Chemotherapy Evaluation Program, Division of Cancer Treatment, National Cancer Institute (Revised August 1974). Pages 31 and 32 thereof concern the formulation of cisplatin supplied gratis by the N.C.I. to clinicians for their clinical evaluation in the chemotherapy of cancer and read as follows:

| PHARMACEUTICAL DATA SHEET NSC-119875 Cis-Diamminedichloroplatinum (II) | |
|---|---|
| Dosage Formulation | |
| 10 mg./vial | The contents of each 20 ml. flint vial appears as an off-white lyophilized cake. Each vial contains 10 mg. of NSC-119875; 90 mg. of Sodium Chloride; 100 mg. of Mannitol and Hydrochloric acid for pH adjustment. |
| Solution Preparation | |
| 10 mg./vial | When reconstituted with 10 ml. of Sterile Water for Injection, USP, each ml. of the resulting solution will contain 1 mg. of NSC-119875, 10 mg. of Mannitol, and 9 mg. of Sodium Chloride having a pH range of 3.5–4.5. |
| Storage | The dry, unopened vials should be stored at refrigeration temperatures (4–8° C.). |
| Stability | Intact vials have a provisional stability of one year when stored at refrigeration temperature (4–8° C.). Stability recommendations may be adjusted pending completion |

-continued

PHARMACEUTICAL DATA SHEET
NSC-119875 Cis-Diamminedichloroplatinum (II)

| | |
|---|---|
| | of a two-year shelf-life study. Reconstitution as recommended results in a pale, yellow solution which is stable for not more than one hour at room temperature (22° C.) when exposed to normal room illumination and not more than eight hours at room temperature (22° C.) when protected from light. Reconstituted solutions may form a precipitate after one hour at refrigeration temperature (4-8° C.). |
| Caution | The lyophilized dosage formulations contain no preservatives and therefore it is advised to discard solutions eight hours after reconstitution. |

August, 1974
Clinical Drug Distribution Section
Drug Development Branch

Published United Kingdom Patent Application No. 2,021,946A describes stable aqueous solutions of cisplatin having a concentration of cisplatin between about 0.1 and 1.0 mg/ml and a pH in the range of 2.0 to 3.0. The solutions may also contain a nontoxic, pharmaceutically acceptable, inorganic source of chloride ions, such as sodium chloride, and an excipient such as mannitol.

COMPLETE DISCLOSURE

This invention relates to stable, concentrated, solutions of cisplatin having concentrations of from about 2.5 to about 25 mg/ml. More particularly, the invention relates to stable, concentrated solutions of cisplatin in a solvent medium comprising from about 30% to about 95% polyethylene glycol having an average molecular weight of from about 150 to about 9000 or a methoxy polyethylene glycol having an average molecular weight of from about 300 to about 6000, or a mixture thereof, and from about 5% to about 70% water, said solutions also containing at least one nontoxic, pharmaceutically acceptable source of chloride ion in an amount which is at least about equivalent to the amount of cisplatin present in the solution, and said solutions having a cisplatin concentration of from about 2.5 to about 25 mg/ml.

Stable aqueous solutions of cisplatin have been described in published United Kingdom Patent Application No. 2,021,946A. Although stable solutions containing cisplatin concentrations up to about 1 mg/ml may be obtained in such aqueous media at room temperature, crystallization of the cisplatin may occur in the cold at cisplatin concentrations substantially above about 0.5 mg/ml. Redissolving such crystallized cisplatin is not readily accomplished by shaking at room temperature, although a solution may be re-obtained by heating to about 37° C. Since shipping and storage temperatures after sale cannot be controlled, and crystallization of cisplatin in the vials would create an undesirable problem for the administering physician, the maximum practical concentration of cisplatin in such aqueous media is about 0.5 mg/ml.

The cisplatin solutions of the present invention may contain up to about 25 mg of cisplatin per ml, although the preferred maximum is about 15 mg/ml. Solutions of the present invention containing 15 mg of cisplatin per ml have been maintained at a temperature of 4° C. for 12 months without crystallization of cisplatin. Such solutions have also been frozen at −60° C. and then thawed at room temperature with no evidence of cisplatin precipitation. Thus, practical solutions prepared according to the present invention may have cisplatin concentrations at least 30 times higher than practical aqueous solutions prepared according to the prior art.

It will be appreciated that the concentrated solutions of cisplatin provided by the present invention will require lower shipping, storage and other costs per unit dose when compared to the known aqueous solutions. Although the known lyophilized solid form also has lower shipping and storage costs, that saving is more than offset by the time and expenses involved in lyophilization.

In a preferred embodiment of the present invention, the solvent medium comprises from about 80% to about 95% (and more preferably from about 85% to about 90%) polyethylene glycol having an average molecular weight of from about 250 to about 1600 (and more preferably from about 250 to about 650) and from about 5% to about 20% (and more preferably from about 10% to about 15%) water. In a most preferred embodiment the solvent medium comprises about 90% polyethylene glycol having an average molecular weight of from about 350 to about 450 and about 10% water.

Preferably the solution contains from about 5 to about 20 mg of cisplatin per ml and most preferably from about 10 to about 15 mg/ml. The nontoxic, pharmaceutically acceptable source of chloride ion preferably is present in a concentration of at least about two equivalents per equivalent of cisplatin in the solution. Concentrations as high as 50 equivalents or more of chloride ion per equivalent of cisplatin may be utilized, depending on the cisplatin concentration, the percentage of water present and the particular source of chloride ion, but such high concentrations of chloride ion usually are neither necessary nor desirable. It will be appreciated by those skilled in the art that, with a high cisplatin concentration and a low water content, it would not be possible to dissolve a sufficient amount of a chloride ion source such as sodium chloride to provide 50 equivalents of chloride ion per equivalent of cisplatin. Further, a saturated, or nearly saturated solution of an inorganic chloride salt would be undesirable because of the possibility of crystallization from the solution in the cold. In the situation set forth above, 50 equivalents of chloride ion per equivalent of cisplatin could be obtained by the use of hydrochloric acid as the source of chloride ion, but this might give a solution having an undesirably high acidity, i.e. low pH. We have found that excessively acidic solutions are somewhat less stable than more moderately acidic solutions. The pH range of the solutions preferably is from about 1.5 to about 4.5. We prefer to utilize from about 2 to about 10 equivalents of chloride ion per equivalent of cisplatin, and most preferably from about 3 to about 7 equivalents of chloride ion per equivalent of cisplatin.

The chloride ion may be provided by the addition of hydrochloric acid, a nontoxic pharmaceutically metallic halide such as sodium chloride, potassium chloride, calcium chloride or magnesium chloride, or the hydrochloric acid addition salt of a nontoxic pharmaceutically acceptable tertiary amine such as triethylamine, or by mixtures thereof. The preferred source of chloride ion is hydrochloric acid, sodium chloride or a mixture thereof.

Polyethylene glycols and methoxy polyethylene glycols have the general formulae

and

respectively, and are commercially available as CARBOWAX Polyethylene Glycols and CARBOWAX Methoxy Polyethylene Glycols. We prefer to utilize the SENTRY Grades of CARBOWAX Polyethylene Glycols, which are produced to meet U.S.P., N.F. and F.C.C. specifications for food and drug applications. Typical molecular weight ranges for a variety of CARBOWAX Polyethylene Glycols and CARBOWAX Methoxy Polyethylene Glycols are given in Tables 1 and 2.

TABLE 1

| CARBOWAX Polyethylene Glycols | Typical Molecular Weight Range |
|---|---|
| 200 | 190 to 210 |
| 300 | 285 to 315 |
| 400 | 380 to 420 |
| 600 | 570 to 630 |
| 1000 | 950 to 1050 |
| 1540 | 1300 to 1600 |
| 4000 | 3000 to 3700 |
| 6000 | 7000 to 9000 |

TABLE 2

| CARBOWAX Methoxy Polyethylene Glycols | Typical Molecular Weight Range |
|---|---|
| 350 | 335 to 365 |
| 550 | 525 to 575 |
| 750 | 715 to 785 |
| 2000 | 1850 to 2150 |

Polyethylene glycols are known to form complexes with certain inorganic salts. Thus, the reaction of polyethylene glycols with ammonium cobalt thiocyanate to form a blue complex is the basis of one colorimetric method of determining the concentration of polyethylene glycols in various mixtures. We believe that the unique stability of cisplatin in the solutions of the present invention may be due to a complex formed between the cisplatin and the polyethylene glycol, but this is only theory and does not form a part of the invention. Evidence of complex formation has been noted in our TLC procedure. Using techniques described below, aqueous cisplatin produces a spot at about Rf 0.65. However, a solution of cisplatin in 90% Polyethylene Glycol 400—10% H$_2$O (or 10% 0.5 N HCl) gives a spot at about Rf 0.3 which streaks to about Rf 0.65. Dilution with substantial quantities of water appears to immediately break the complex, since dilution of the above PEG-H$_2$O (or HCl) solution with five volumes of water then shows only a cisplatin spot at about Rf 0.65.

Thin Layer Chromatography

Apparatus and Reagents
(a) TLC plates—EM Laboratories silica gel 60 plates, Catalog No. 5763, or equivalent.
(b) Eluent—Acetone:1 N HNO$_3$ (9:1). Prepare fresh daily.
(c) Developer—Dissolve 5.6 gm of stannous chloride in 10 ml concentrated HCl. Add 90 ml of distilled water and 0.2 gm of KI. Mix well. Prepare fresh daily.
(d) Laboratory oven set to 100° C.

Procedure
(a) Dilute the sample with 5 volumes of dimethylformamide (DMF) [Burdick and Jackson, distilled in glass].
(b) Spot a TLC plate with 5 microliters of the sample and 5 microliters of a standard solution containing cisplatin (and transplatinum and platinum B, if appropriate) at a concentration approximately the same as that expected in the sample being analyzed. Develop a height of 10 cm in a TLC tank preequilibrated with the eluent. Spray the dried plate with freshly prepared developer solution and place it in a 100° C. oven for 10 minutes. Observe the yellow/purple zones.
(c) Approximate Rf values:
0.65—cisplatin
0.76—transplatinum
0.9—platinum B.

HPLC assays of the solutions of this invention for cisplatin content may be conducted according to the procedure described in our colleagues' published United Kingdom Patent Application No. 2,021,946A. The preferred mobile phase is ethyl acetate/methanol/-dimethylformamide/distilled water (25/16/5/5). The standard preferably is cisplatin dissolved in dimethylformamide at a concentration of 1 mg/ml. Samples for analysis are diluted with dimethylformamide to an approximate cisplatin concentration of 1 mg/ml.

Although no particular advantage is obtained by their presence, the solutions of this invention may, if desired, contain a customary, physiologically acceptable excipient such as mannitol.

Based on stability studies to date, the predicted stability of the solutions of this invention (defined as a 10% loss of potency) is in excess of two years at room temperature.

In a preferred embodiment of this invention, the solutions are sterile and pyrogen-free, and are packaged in sterile, pyrogen-free containers. Such solutions may then be diluted with, for example, Sterile Water for Injection, U.S.P., or Sterile Normal Saline Solution, U.S.P., and administered by the intramuscular or intravenous route. Means for sterilizing these solutions are well known in the art. We prefer to pass the solutions through a sterile, pyrogen-free 0.22 micron Millipore filter, using aseptic techniques, under sterile nitrogen pressure. Millipore is a registered trademark of the Millipore Corporation for membrane filters. The sterile filtrate is collected in sterile, pyrogen-free containers and is ultimately filled, in the desired amount, into suitable sterile, pyrogen-free vials, stoppered with sterile, pyrogen-free stoppers (preferably teflon coated) and sealed with sterile aluminum seals.

For use in the treatment of cancer, the concentrated solutions are diluted to the desired concentration (typically 1 mg cisplatin per ml) with, for example, Sterile Water for Injection, U.S.P., Sterile Normal Saline Solution, U.S.P., or Sterile Glucose Solution and used by intramuscular or intravenous injection, or intravenous infusion as known for prior art cisplatin preparations. Currently used dosages with mild to moderately acceptable toxicity are in the range of 60–100 mg/M² intravenously as a single dose or divided over 3–5 days, to be repeated at 4-week intervals. A dosage of 60 mg/M² is roughly equal to 1.5 mg/kg which in turn is roughly equal to 105 mg/patient weighing 70 kg. Frequently, use is made of concurrent therapy with other chemotherapeutic agents for best results.

As used herein and in the claims, references to "equivalents" of chloride ion per "equivalent" of cisplatin means molar equivalents. Thus, for example, when utilizing the preferred range of from about 3 to about 7 equivalents of chloride ion per equivalent of cisplatin, one would utilize from about 3 to about 7 moles of NaCl per mole of cisplatin but from about 1.5 to about 3.5 moles of $CaCl_2$ per mole of cisplatin, etc.

Platinum B is an arbitrary designation used herein for an acid reaction product of cisplatin which is one-half of the known Magnus red complex and has been tentatively assigned the following structure:

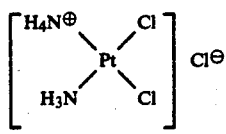

This invention is illustrated by, but is in no way limited to, the following Examples.

EXAMPLE 1

Stable Concentrated Solution of Cisplatin (10 mg/ml) in 90% Polyethylene Glycol 400—10% 1 N HCl Cisplatin (500 mg) was slurried in a solution of 5 ml of 1 N HCl and 45 ml of Polyethylene Glycol 400. After 2.5 days of stirring at room temperature (with the container protected from light with aluminum foil) a clear yellow solution was obtained. Aliquots of the solution were placed in 17 ml amber vials, stoppered with teflon coated stoppers, sealed with aluminum caps and placed on storage stability tests at various temperatures. After two weeks' storage at 45° C., thin layer chromatography (TLC) indicated the presence of a trace of transplatinum and approximately 1% platinum B. After two weeks' storage at 56° C., TLC indicated the presence of <1% transplatinum and approximately 3% platinum B. Samples stored for two weeks at 56° C. were diluted with 4, 9 and 19 volumes of water to give clear solutions containing 2, 1 and 0.5 mg/ml, respectively, of cisplatin. A slight cloudiness developed in each of the diluted samples after standing approximately 18 hours at room temperature.

EXAMPLE 2

Stable Concentrated Solution of Cisplatin (10 mg/ml) in 90% Polyethylene Glycol 400—10% 0.5 N HCl Five ml of purified water U.S.P. and 5.0 ml of 1 N HCl were mixed and 90.0 ml of Polyethylene Glycol 400 was added. To 50 ml of the above solution was added 500 mg of cisplatin and the mixture was protected from light with aluminum foil and stirred at room temperature for 24 hours to produce a clear solution. TLC of the freshly prepared solution showed only a cisplatin zone with a possible trace of transplatinum. Two ml aliquots of the solution were placed in 17 ml amber vials, stoppered with teflon coated stoppers, sealed with aluminum caps and placed on storage stability tests at various temperatures. One sample vial was frozen in a dry ice-acetone bath for one hour and then allowed to come to room temperature. A clear solution was obtained, with no evidence of a precipitate. After three months' storage at both 37° C. and 45° C., TLC indicated the presence of 1–2% platinum B and a possible trace of transplatinum. After one month storage at 56° C., TLC indicated the presence of more than 5% but less than 10 % of platinum B and a trace of transplatinum. Samples stored at 37° C. and 45° C. for three months and at 56° C. for one month were diluted with four volumes of purified water U.S.P. to give clear solutions containing 2 mg/ml of cisplatin. The diluted solutions remained clear after standing 24 hours at room temperature.

EXAMPLE 3

Stable Concentrated Solution of Cisplatin (10 mg/ml) Plus $CaCl_2$ (20 mg/ml) in 90% Polyethylene Glycol 400—10% 0.5 N HCl Two gms of reagent grade anhydrous $CaCl_2$ was dissolved in a mixture of 5 ml purified water U.S.P. and 5 ml 1 N HCl. Polyethylene Glycol 400 (89 ml) was added to bring the volume to 100 ml. To 50 ml of this solution was added 550 mg of cisplatin, and the mixture was protected from light with aluminum foil and stirred at room temperature for 24 hours to give a clear solution. TLC of the freshly prepared solution indicated only a cisplatin zone with a possible trace of transplatinum. Two ml aliquots of the solution were placed in 17 ml amber vials, stoppered with teflon coated stoppers, sealed with aluminum caps and placed on storage stability tests at various temperatures. One sample vial was placed in a dry ice-acetone bath for 0.5 hour and froze to a clear gel. It was then allowed to come to room temperature and a clear solution was obtained. After three months' storage at 37° C., TLC indicated the presence of 1–2% platinum B and a possible trace of transplatinum. After three months' storage at 45° C., TLC indicated the presence of approximately 5% platinum B and a possible trace of transplatinum. After one month storage at 56° C., TLC indicated the presence of 8–10% platinum B and a trace of transplatinum. Samples stored at 37° C. and 45° C. for three months and at 56° C. for one month were diluted with four volumes of purified water U.S.P. to give clear solutions containing 2 mg/ml of cisplatin. The diluted solutions remained clear after standing 24 hours at room temperature.

EXAMPLE 4

Stable Concentrated Solution of Cisplatin (Approximately 22 mg/ml) Plus $CaCl_2$ (25 mg/ml) in 90% Polyethylene Glycol—10% 0.5 N HCl To three ml of a solution of 90% Polyethylene Glycol 400 and 10% 0.5 N HCl was added 45 mg of cisplatin, and the mixture was stirred for about one hour at room temperature to obtain a clear solution. An additional 30 mg of cisplatin was added (total of 25 mg/ml) and the mixture was stirred at about 45° C. for one hour and then at room temperature for 18 hours to produce a nearly complete solution. The small amount of insoluble material was removed by filtration. TLC of the filtrate showed only a cisplatin zone with a possible trace of transplatinum. The remainder of the filtrate was placed in a 17 ml amber vial, stoppered with a teflon coated stopper, sealed with an aluminum cap and held at 45° C. for three months. After aging three months at 45° C., TLC indicated the presence of 1-2% platinum B and no transplatinum. Dilution of the aged solution with purified water U.S.P. to a concentration of 2 mg/ml of cisplatin gave clear solutions, which remained clear after standing at room temperature for 24 hours.

EXAMPLE 5

Stable Concentrated Solution of Cisplatin (12 mg/ml) Plus NaCl (10 mg/ml) in 90% Polyethylene Glycol 400—10% 0.5 N HCl Sodium chloride (100 mg) was dissolved in a solution of 5 ml purified water U.S.P. and 5 ml 1 N HCl. To this solution was added 90 ml of Polyethylene Glycol 400 and the mixture was stirred for 15 minutes. To 50 ml of the latter solution was added 500 mg of cisplatin, and the mixture was stirred in the dark at room temperature for 3 days to produce a clear solution. TLC of the freshly prepared solution showed only a cisplatin spot. High performance liquid chromatography (HPLC) assay of the freshly prepared solution showed it to contain 12 mg of cisplatin per ml. Aliquots were sealed in 17 ml amber vials as described in Example 3 and put on storage stability tests at various temperatures. After storage at 37° C. for three months, TLC indicated the presence of less than 1% platinum B and no transplatinum. After storage at 56° C. for one month, TLC indicated the presence of 1-2% platinum B and no transplatinum. Dilution of the aged samples with purified water U.S.P. to a concentration of 2 mg/ml of cisplatin gave clear solutions, which remained clear after standing at room temperature for 24 hours.

HPLC assays of samples stored 3 months at 45° C., 6 months at 37° C. and 8 months at room temperature showed potency losses of 6.6%, 6.1% and 2.3%, respectively.

EXAMPLE 6

Stable Concentrated Solution of Cisplatin (11.4 mg/ml) Plus NaCl (10 mg/ml) in 90% Polyethylene Glycol 400—10% Water To a solution of 50 mg NaCl in 5 ml of purified water U.S.P. and 45 ml Polyethylene Glycol 400 was added 500 mg of cisplatin, and the mixture was stirred in the dark at room temperature for 6 hours to give a clear solution. TLC of the freshly prepared solution showed only a cisplatin spot; HPLC assay showed it to contain 11.4 mg of cisplatin per ml. Aliquots were sealed in 17 ml amber vials as described in Example 3 and put on storage stability tests at various temperatures. After storage at 37° C. and 45° C. for 3 months, TLC indicated the presence of 1% platinum B and no transplatinum. After storage at 56° C. for one month, TLC indicated the presence of 2-3% platinum B and no transplatinum. Dilution of the aged samples with purified water U.S.P. to a concentration of 2 mg/ml of cisplatin gave clear solutions, which remained clear after standing at room temperature for 24 hours.

HPLC assays of samples stored 3 months at 45° C., 6 months at 37° C. and 7 months at room temperature showed potency losses of 6.1%, 7.0% and 0.9%, respectively.

EXAMPLE 7

Stable Concentrated Solution of Cisplatin (10 mg/ml) in 90% Polyethylene Glycol 600—10% 0.5 N HCl To a solution of 2.5 ml of purified water U.S.P., 2.5 ml of 1 N HCl and 45 ml of Polyethylene Glycol 600 was added 500 mg of cisplatin, and the mixture was stirred in the dark at room temperature for 5 hours to obtain a clear solution. TLC of the freshly prepared solution showed only a cisplatin spot. Samples of the freshly prepared solution were diluted with 1, 2, 3, 4, 5 and 9 volumes of purified water U.S.P.; these diluted solutions showed no crystallization after standing for 16 hours at room temperature or 4° C. Aliquots of the freshly prepared solution were sealed in 17 ml amber vials as described in Example 3 and were put on storage stability tests at various temperatures. After storage at 37° C. and 45° C. for 3 months, TLC indicated the presence of 1% platinum B and no transplatinum. After storage at 56° C. for one month, TLC indicated the presence of 3.4% platinum B and no transplatinum. Dilution of the aged samples with purified water U.S.P. to a concentration of 2 mg/ml of cisplatin gave clear solutions, which remained clear after standing at room temperature for 24 hours.

EXAMPLE 8

Stable Concentrated Solution of Cisplatin (10 mg/ml) Plus NaCl (10 mg/ml) in 90% Polyethylene Glycol 400—10% 0.2 N HCl To a solution of 0.5 gm NaCl in 4 ml of purified water U.S.P., 1 ml of 1 N HCl and 45 ml of Polyethylene Glycol 400 was added 250 mg of cisplatin, and the mixture was stirred in the dark at room temperature for 4 hours to give a clear yellow solution. TLC of the freshly prepared solution showed only a cisplatin spot. Dilutions of the freshly prepared solution with 1, 2, 3, 4, 5 and 9 volumes of purified water gave clear solutions which remained clear after standing at room temperature for 24 hours. The 1, 2, 3, 4 and 5 volume dilutions showed no crystallization when held at 4° C. for 24 hours. Aliquots of the freshly prepared solution were sealed in 17 ml amber vials as described in Example 3 and were put on storage stability tests at various temperatures. After storage at 37° C. for three months, TLC indicated the presence of 1% platinum B with a possible trace of transplatinum. After storage at 45° C. for three months, TLC indicated the presence of 5% platinum B with a possible trace of transplatinum. After storage at 56° C. for one month, TLC indicated the presence of 2-3% platinum B and no transplatinum. Dilution of the aged samples with purified water U.S.P. to a concentration of 2 mg/ml of cisplatin gave clear solutions which remained clear after standing for 24 hours at room temperature.

EXAMPLE 9

Stable Concentrated Solution of Cisplatin (2.5 mg/ml), NaCl (9 mg/ml) and Mannitol (12.5 mg/ml) in Acidified 31% (w/v) Aqueous Polyethylene Glycol 6000

Sodium chloride (0.9 gm), mannitol (1.25 gm) and Polyethylene Glycol 6000 (31.3 gms) were dissolved in sufficient purified water U.S.P. to make 100 ml of solution, and the solution was then acidified to pH 2.2 with 1 N HCl (0.7 ml). Cisplatin (255 mg) was added and the mixture was stirred in the dark for 3 days at room temperature to obtain a clear solution. TLC of the freshly prepared solution showed only a cisplatin zone. Aliquots of the freshly prepared solution were sealed in 17 ml amber vials as described in Example 3 and were put on storage stability tests at 45° C. and 56° C. After storage for two months at 45° C. and 56° C., TLC showed less than 1% platinum B and no transplatinum. Dilution of the aged samples with an equal volume of purified water U.S.P. gave clear solutions which remained clear after standing at room temperature for 24 hours.

EXAMPLE 10

Stable Concentrated Solution of Cisplatin (15.8 mg/ml) Plus NaCl (10 mg/ml) in 90% Aqueous Polyethylene Glycol 400

Polyethylene Glycol 400 (90 ml) was dissolved in a solution of 1.0 gm NaCl in 10 ml purified water U.S.P. To 60 ml of the resulting solution was added 900 mg of cisplatin, and the mixture was stirred in the dark for five hours at room temperature to obtain a clear solution. TLC of the freshly prepared solution showed only a cisplatin zone; HPLC assay showed it to contain 15.8 mg of cisplatin per ml. Dilution of the freshly prepared solution with four volumes of purified water U.S.P. gave a clear solution which remained clear after standing at room temperature for 24 hours. Aliquots of the freshly prepared solution were sealed in 17 ml amber vials as described in Example 3 and put on storage stability tests at various temperatures. After two months' storage at 45° C., TLC indicated 1.5% platinum B and no transplatinum. After one month storage at 56° C., TLC indicated 2% platinum B and no transplatinum. The sample aged at 56° C. was diluted to a concentration of 2 mg/ml with sterile water for injection and the sample aged at 45° C. was diluted to concentrations of 2.5 and 5.0 mg/ml of cisplatin with sterile water for injection. They each formed clear solutions which remained clear after standing at room temperature for 24 hours.

HPLC assays of samples stored 3 months at 45° C., 6 months at 37° C. and 8 months at room temperature showed potency losses of 7.6%, 7.6% and 0%, respectively.

EXAMPLE 11

Stable Concentrated Solution of Cisplatin (15 mg/ml) Plus $CaCl_2$ (25 mg/ml) in 90% Aqueous Polyethylene Glycol 400

To a solution of 2.5 gms of $CaCl_2$ in 10 ml of purified water U.S.P. was added 90 ml of Polyethylene Glycol 400, and the resulting solution was stirred for ten minutes. To 50 ml of the above solution was added 750 mg of cisplatin and the mixture was stirred for 5 hours in the dark at room temperature to give a clear solution. TLC of the freshly prepared solution showed only a cisplatin zone. Dilutions of the freshly prepared solution with 1, 2, 5 and 10 volumes, respectively, of purified water U.S.P. gave clear solutions. Aliquots of the freshly prepared solution were sealed in 17 ml amber vials as described in Example 3 and put on storage stability at 45° C. and 56° C. After two months' storage at 45° C., TLC indicated the presence of 1.5% platinum B and no transplatinum. After one month storage at 56° C., TLC indicated the presence of 2.5-5% platinum B and no transplatinum. The sample aged at 56° C. was diluted to a concentration of 2 mg/ml, and the sample aged at 45° C. was diluted to concentrations of 2.5 and 5.0 mg/ml, of cisplatin with sterile water for injection. They formed clear solutions which remained clear after standing at room temperature for 24 hours.

EXAMPLE 12

Sterile, Stable, Concentrated Solution of Cisplatin in 90% Polyethylene Glycol 400—10% 0.5 N HCl (Label claim is 15 mg/ml of cisplatin activity)

NOTE: Cisplatin is a possible carcinogen. Protective clothing, gloves, masks, eyeglasses and head covering must be worn during the entire procedure. All work areas and equipment must be thoroughly cleaned to avoid any future contamination.

| FORMULA | | |
|---|---|---|
| | Per ml | Per 10.0 ml |
| Cisplatin | 0.015 gm[1] | 0.150 gm |
| Sodium Chloride | 0.015 gm | 0.150 gm |
| 0.5N Hydrochloric Acid[2] | 0.10 ml | 1.0 ml |
| Polyethylene Glycol 400 (SENTRY grade) | q.s. to 1.0 ml | q.s. to 10.0 ml |

[1]This weight of cisplatin assumes a potency of 1000 mcg/mg. To determine the amount of cisplatin required use the following formula:
$$\frac{1000 \times 0.015 \text{ gm}}{\text{Potency of cisplatin in mcg/mg}} = \text{Grams of cisplatin required}$$

[2]One liter of 0.5N hydrochloric acid is prepared as follows:
1. Place 957.25 ml of Sterile Water for Injection, U.S.P. in a clean one liter Erlenmeyer flask.
2. With rapid stirring, slowly and cautiously add 42.75 ml of concentrated hydrochloric acid. Stir for 10 minutes. Stopper with a clean butyl rubber stopper.

MANUFACTURING INSTRUCTIONS FOR ONE LITER OF STERILE SOLUTION

1. Place 100 ml of 0.5 N hydrochloric acid in a clean, calibrated 1-liter Erlenmeyer flask containing a suitable stirrer, such as a 6 cm magnetic, teflon coated stirrer bar.
2. Add, with moderate stirring, 15.0 grams of sodium chloride. Stir until the salt is completely dissolved.
3. Add with rapid stirring 750 ml of Polyethylene Glycol 400 (SENTRY grade) and stir for 5 minutes.
4. Remove the magnetic stirrer bar and drain excess fluid back into the flask.
5. Cautiously add 15.0 grams of cisplatin activity.
6. Add Polyethylene Glycol 400 (SENTRY grade) to the 1 liter mark (a total of 880 ml of Polyethylene Glycol 400 required).
7. Place the teflon stirrer bar back into the mixture and stopper with a clean butyl rubber stopper.
8. Wrap the flask in aluminum foil to exclude all light.
9. Rapidly stir for 24–48 hours at ambient room temperature. A clear solution should be obtained. If a clear solution is not obtained in 48 hours, the mixture may be warmed to 37°-40° C. for 2-6 hours in the absence of air and light to facilitate rapid solution of the remaining cisplatin. Cool to 23°-27° C.
10. Using aseptic technique, pass the dark yellow solution under proper sterile nitrogen pressure, through a suitable sterile, pyrogen-free 0.22 micron Millipore filter. Collect the sterile filtrate in a sterile, pyrogen-free Erlenmeyer flask. Stopper with a sterile, pyrogen-free butyl rubber stopper. The solution may be stored in the dark.
11. Fill the required amount of sterile solution into sterile, pyrogen-free amber vials. Stopper with sterile, pyrogen-free teflon stopper. Seal with sterile aluminum seals.
12. The vials should contain the following precautionary label:

NOT FOR DIRECT INTRAMUSCULAR OR INTRAVENOUS USE*

*The PEG-400 solution may be diluted with 14 parts of Sterile Water for Injection, U.S.P. or Sterile Normal Saline Solution, U.S.P. to give a 1 mg/ml solution of cisplatin. If higher concentrations are required, proportionally less Sterile Water or Saline Solution may be used. The diluted solutions may be used intravenously and are stable at room ambient temperature (22°-26° C.) for at least 48 hours. Do not refrigerate diluted solutions as crystals may form.

13. Store the vials in the dark.

EXAMPLE 13

Stable Concentrated Solution of Cisplatin (2.5 mg/ml), NaCl (9 mg/ml), CaCl$_2$ (15 mg/ml) and Mannitol (10 mg/ml) in Acidified 31% Aqueous Polyethylene Glycol 400

Sodium chloride (0.9 gm), CaCl$_2$ (1.5 gm) and mannitol (1.0 gm) were dissolved in a mixture of 31.25 ml Polyethylene Glycol 400 and 40 ml purified water U.S.P. The solution was acidified to pH 2.2 with 1 N HCl (0.4 ml), 255 mg of cisplatin was added, the volume was brought to 100 ml with purified water U.S.P., and the mixture was stirred in the dark for 5 hours at room temperature to obtain a clear solution. TLC of the freshly prepared solution showed only a cisplatin zone.

EXAMPLE 14

The general procedure of Example 5 is repeated except that the sodium chloride utilized therein is replaced by an equivalent amount of magnesium chloride, and a stable concentrated solution of cisplatin is thereby produced.

EXAMPLE 15

The general procedure of Example 5 is repeated except that the sodium chloride utilized therein is replaced by an equivalent amount of triethylamine hydrochloride, and a stable concentrated solution of cisplatin is produced.

EXAMPLE 16

The general procedure of Example 5 is repeated except that the Polyethylene Glycol 400 utilized therein is replaced by an equal volume of Polyethylene Glycols 200 and 300, respectively, and stable concentrated solutions of cisplatin are produced.

EXAMPLE 17

The general procedure of Example 9 is repeated except that the Polyethylene Glycol 6000 utilized therein is replaced by an equal weight of Polyethylene Glycols 1000 and 4000, respectively, and stable concentrated solutions of cisplatin are produced.

We claim:

1. A sterile, stable, concentrated solution of cisplatin in a sealed container, said solution containing from about 10 to about 15 mg of cisplatin per ml and from about 10 to about 15 mg of NaCl per ml in a solvent medium consisting of about 90% of a polyethylene glycol having an average molecular weight of from about 350 to about 450 and about 10% water.

2. A sterile, stable, concentrated solution of cisplatin in a sealed container, said solution containing from about 10 to about 15 mg of cisplatin per ml and from about 10 to about 15 mg of NaCl per ml in a solvent medium consisting of about 90% of a polyethylene glycol having an average molecular weight of from about 350 to about 450 and about 10% dilute hydrochloric acid having a concentration up to about 0.5 N.

3. A stable, concentrated solution of cisplatin in a solvent medium comprising from about 85% to about 95% polyethylene glycol having an average molecular weight of from about 350 to about 450 and from about 5% to about 15% water, said solution also containing a source of chloride ion selected from the group consisting of hydrochloric acid, sodium chloride and a mixture thereof, in an amount which is in the range of from about two to about seven equivalents per equivalent of cisplatin in the solution, and said solution having a cisplatin concentration of from about 5 to about 20 mg/ml.

* * * * *